United States Patent
Holder

(10) Patent No.: US 8,652,062 B1
(45) Date of Patent: Feb. 18, 2014

(54) MULTI-ELECTRONIC NECKLACE

(76) Inventor: Addam Holder, Metropolis, IL (US)

( * ) Notice: Subject to any disclaimer, the term of this patent is extended or adjusted under 35 U.S.C. 154(b) by 0 days.

(21) Appl. No.: 13/200,963

(22) Filed: Oct. 5, 2011

(51) Int. Cl.
*A61B 5/02* (2006.01)
(52) U.S. Cl.
USPC ........................................................... 600/508
(58) Field of Classification Search
USPC ........................................................... 600/508
See application file for complete search history.

(56) References Cited

U.S. PATENT DOCUMENTS

| | | | |
|---|---|---|---|
| 2006/0251283 A1* | 11/2006 | Yeh | 381/388 |
| 2007/0053523 A1* | 3/2007 | Iuliis et al. | 381/77 |
| 2007/0242424 A1* | 10/2007 | Lieu et al. | 361/686 |
| 2008/0047996 A1* | 2/2008 | Blouin | 224/579 |

* cited by examiner

*Primary Examiner* — Joseph Dietrich
(74) *Attorney, Agent, or Firm* — R K Thomson

(57) ABSTRACT

A multi-function electronic necklace includes an Mp3 player with built in wifi connectivity and GPS voice-command in a uniformly dimensioned lanyard which passes simply for a decorative necklace. The necklace includes a microphone and a receptacle for attachment of a Bluetooth headset.

7 Claims, 2 Drawing Sheets

MULTI-ELECTRONIC NECKLACE

BACKGROUND AND SUMMARY OF THE INVENTION

The present invention is directed to the field of electronics. More particularly, the present invention is directed to an electronic necklace which can provide mobile tune player, voice-activated GPS information and wifi connectivity, while appearing to be simply a decorative necklace.

More and more people are carrying devices which allow them to listen to the music of their choice. The device can take the form of an iPod, Mp3 player or the like. The problem is when a person goes into a store, restaurant or other commercial establishment, they set the player down to tend to other items of business and frequently forget to pick up the player.

It is among the objects of the present invention to incorporate an Mp3 player directly into a necklace where it can simply be worn in the manner of any other decorative necklace. This eliminates the problem of walking off without your walkman. The multi-electronic necklace also provides the features of integrated Bluetooth mic in close proximity to the user's mouth; built-in wifi; and a voice command GPS response unit. Alternatively, a portable screen unit can be attached to a receptacle to provide the visual GPS information.

The present invention is a communication necklace comprising a lanyard having a first diameter; an electronic device having a diameter equal to the first diameter, the electronic device including a built in MP3 player and wireless WIFI receiver; a microphone for use with both i. a bluetooth headset, and ii. a voice-command GPS through the WIFI reeiver; c. headphones operable with the lanyard; synchronization means to allow songs to be input to the MP3 player. The synchronization means includes multiple ports to allow music to be input via more than one method. The multiple ports include a USB port and a slot for a SD card. The necklace features rechargeable battery means positioned adjacent the electronic device to power said MP3 player. In addition, a receptacle jack is provided for enabling attachment of the headphones. Alternatively, the headphones can be made integrally with the lanyard and include a pair of ear buds which protrude from an upper portion of said lanyard. The lanyard may also include a heart monitor to enable the wearer to easily determine his/her heart rate during a jog, exercycle, treadmill, or other exercise regimen.

Various other features, advantages, and characteristics of the present invention will become apparent after a reading of the following detailed description.

BRIEF DESCRIPTION OF THE DRAWINGS

The preferred embodiment(s) of the present invention is/are described in conjunction with the associated drawings in which like features are indicated with like reference numerals and in which.

DETAILED DESCRIPTION OF THE PREFERRED EMBODIMENT(S)

Figure 1:
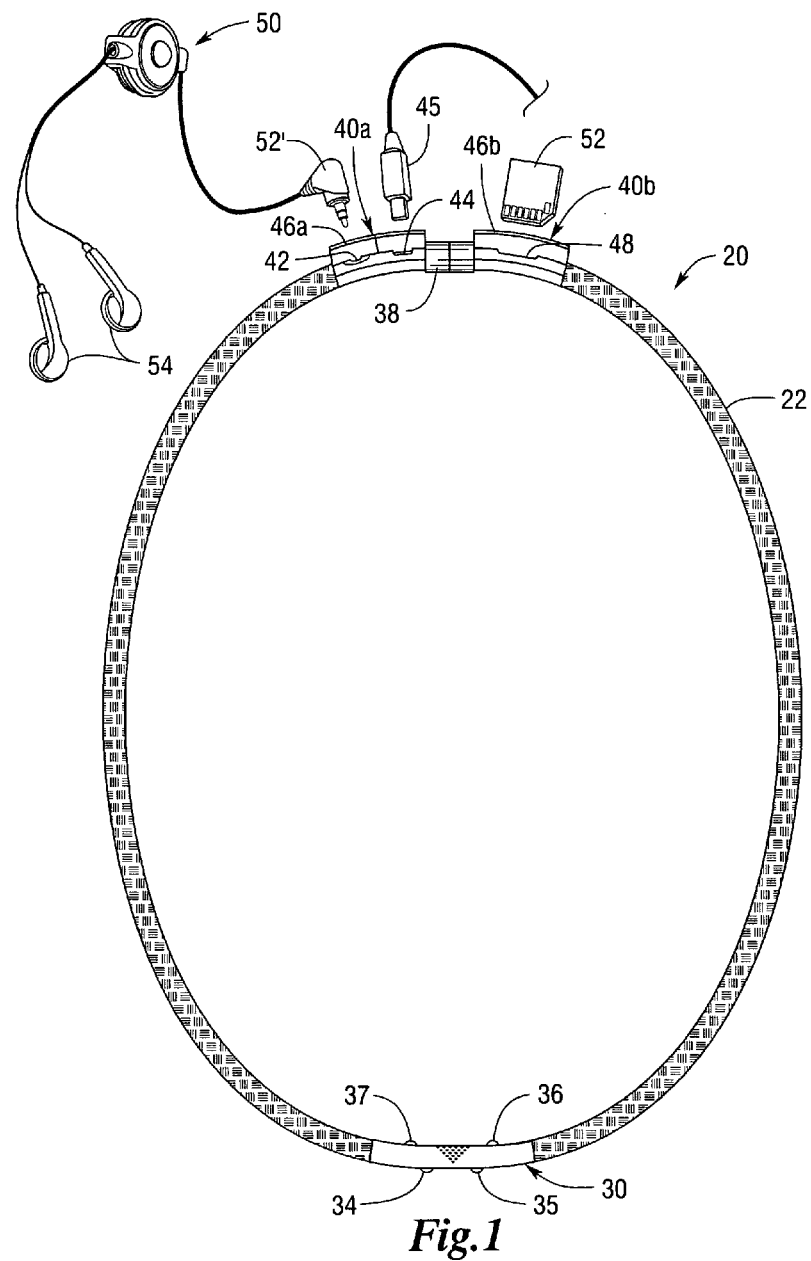
FIG. 1 is a front view of a first embodiment of the multi-electronic device of the present invention; and, FIG. 2 is a second embodiment of the present invention.

A first embodiment of the multi-function electronic device of the present invention is depicted in FIG. 1 generally at 20. Device 20 comprises a lanyard necklace 22 which, in appearance, resembles similar decorative necklaces of this type. Lanyard necklace 22 has a first uniform diameter d and is offered in a plurality of colors to suit individual tastes. Electronic device 30 has the same diameter as lanyard necklace 22 and, unlike a bulky audio device suspended from a chain, does not have significant sway or bounce when the user is walking/jogging. The multi-function device 30 includes an Mp3 player, a Bluetooth and a wifi receiver. A microphone 32 is built in to function as a mouthpiece for the Bluetooth system and a command control for a voice-activated GPS. Device 30 includes a function selection button 34, a volume control button 35, a play button 36 and a pause button 37, for controlling the Mp3 player operation. It will be understood that the selection button 34 will also have settings for GPS and wifi operation. Further, multi-function device 30 can have a heart/pulse rate monitor which, via operation of function selection button 34, provide an announced heart rate to the wearer. Such a feature permits multi-function electronic necklace 20 to be worn during workout periods such as jogging, treadmill, exercycle and other workout regimen, with the Mp3 player affording the wearer tunes appropriate to the activity.

Figure 2:
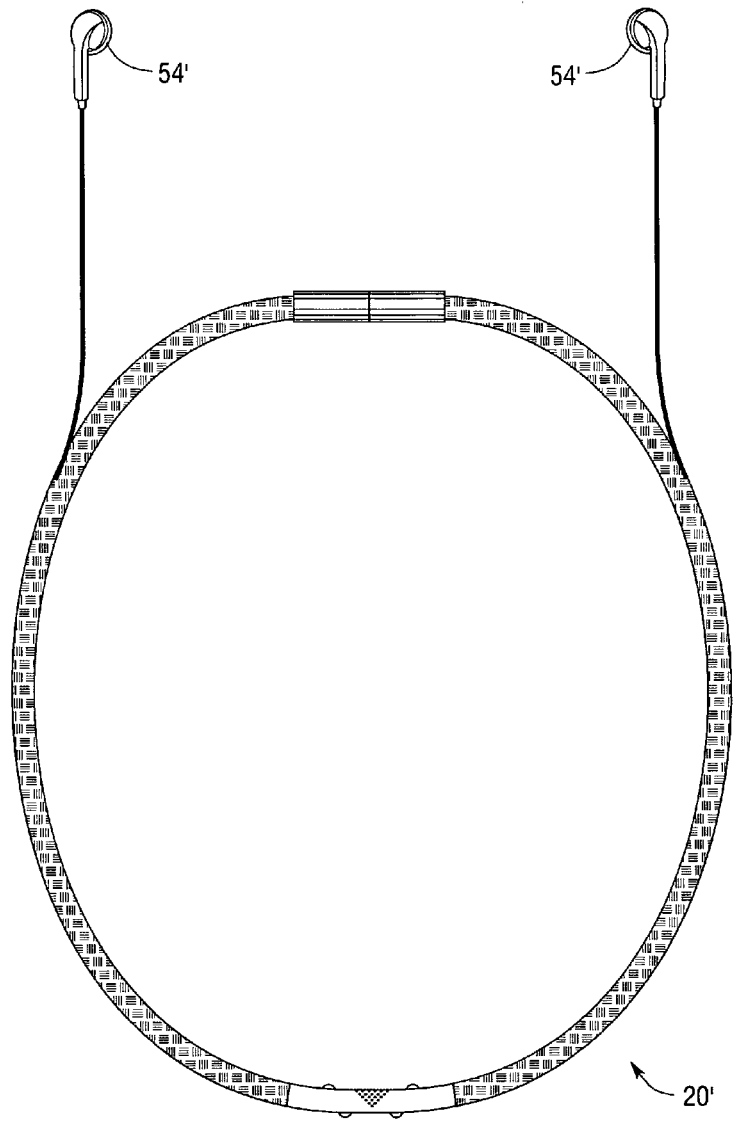

Lanyard necklace 22 incorporates the wiring necessary to interconnect the input/output functions of multi-function device 30 with the input/output elements 40*a*, 40*b* adjacent clasp 38. Element 40*a* includes a of connector port 42 for attachment of Bluetooth head set 50 via jack 52' and a USB port 44 for inputting tunes from an external source via connector 45. Ports 42, 44 are concealed and protected by hinged cover 46*a* when not in use. Bluetooth headset 50 may include retraction unit for ear buds 54 and/or its own controls. Alternatively, the ear buds 54' may be directly incorporated into lanyard necklace 20' (FIG. 2). With the use of simple magnets, ear buds 54' may connect to one another and simply lie behind clasp 38' when not being used. Element 40*b* on the other side of clasp 38 contains a receptacle 48 which can receive an SD card 52 as an alternate method of inputting tunes to the Mp3 player in device 30. USB port 44 can also provide access for connecting a GPS output screen so the voice directions provided by multi-function device 30 can be augmented by a visual input map, or the like. Receptacle 48 is protected by hinged cover 46*b* when not in use. It will be understood that it is the intension of the present invention that the input/output elements 30, 40*a*, 40*b* be the same, or as nearly the same diameter d as lanyard 22 so that, for all intents and purposes, necklace 20 has the same appearance as a simple decorative necklace with a good deal more functionality without the bulky, unwieldiness of a Mp3 player or other musical paraphernalia.

Various changes, alternatives, and modifications will become apparent to a person of ordinary skill in the art after a reading of the foregoing specification. It is intended that all such changes, alternatives, and modifications as fall within the scope of the appended claims be considered part of the present invention.

I claim:

1. A communication necklace comprising
   a. a lanyard having a first diameter and a clasp for securing about a user's neck;
   b. an electronic device having a diameter equal to said first diameter, said electronic device including a built in MP3 player and wireless WIFI receiver;
   c. a microphone for use with both
      i. a bluetooth headset, and
      ii. a voice-command GPS through said WIFI receiver;
   d. headphones operable with said lanyard;
   e. synchronization means to allow songs to be input to said MP3 player;

f. input and output elements positioned adjacent said clasp; and, g. wiring internal to said lanyard interconnecting said input and output elements with said electronic device.

2. The communication necklace of claim 1 wherein said synchronization means includes multiple ports to allow music to be input via more than one method.

3. The communication necklace of claim 2 wherein said multiple ports include a USB port and a slot for a SD card.

4. The communication necklace of claim 1 further comprising rechargeable battery means positioned in said uniform diameter portion to power said MP3 player.

5. The communication necklace of claim 1 further comprising a receptacle jack for enabling attachment of said headphones.

6. The communication necklace of claim 1 wherein said headphones are made integrally with said lanyard and comprise a pair of ear buds which protrude from an upper portion of said lanyard.

7. The communication necklace of claim 1 further comprising a heart monitor for determining heart rate during an exercise period.

* * * * *